United States Patent [19]
Garby et al.

[11] Patent Number: 5,799,651
[45] Date of Patent: *Sep. 1, 1998

[54] INDICATOR DEVICE RESPONSIVE TO AXIAL FORCE

[75] Inventors: Gage Garby; Jeffrey T. Ballas, both of Boulder, Colo.

[73] Assignee: Senetics, Inc., Boulder, Colo.

[*] Notice: The term of this patent shall not extend beyond the expiration date of Pat. No. 5,611,444.

[21] Appl. No.: 779,014

[22] Filed: Jan. 6, 1997

Related U.S. Application Data

[60] Continuation of Ser. No. 412,359, Mar. 29, 1995, Pat. No. 5,611,444, which is a division of Ser. No. 125,365, Sep. 22, 1993, Pat. No. 5,421,482, which is a continuation-in-part of Ser. No. 109,401, Aug. 19, 1993, Pat. No. 5,299,701, which is a continuation of Ser. No. 641,759, Jan. 17, 1991, abandoned, which is a continuation-in-part of Ser. No. 306,485, Feb. 3, 1989, Pat. No. 5,009,338.

[51] Int. Cl.$^6$ ................................. A61M 15/00
[52] U.S. Cl. .................... 128/200.23; 128/205.23; 128/204.18; 128/200.14; 128/200.24
[58] Field of Search ................. 128/204.18, 203.15, 128/203.12, 200.24, 200.23, 200.14, 205.23; 604/58

[56] References Cited

U.S. PATENT DOCUMENTS

| | | | |
|---|---|---|---|
| 3,994,421 | 11/1976 | Hansen | 222/182 |
| 4,668,218 | 5/1987 | Virtanen | 128/203.15 |
| 4,817,822 | 4/1989 | Rand et al. | 222/38 |
| 5,299,701 | 4/1994 | Barker et al. | 215/230 |
| 5,388,572 | 2/1995 | Mulhauser et al. | 128/203.15 |
| 5,482,030 | 1/1996 | Klein | 128/200.23 |
| 5,507,277 | 4/1996 | Rubsamen et al. | 128/200.14 |
| 5,582,162 | 12/1996 | Petersson | 128/203.15 |

*Primary Examiner*—John G. Weiss
*Assistant Examiner*—William J. Deane, Jr.
*Attorney, Agent, or Firm*—Davis, Graham & Stubbs LLP

[57] ABSTRACT

A device to indicate the application of a non-rotative force, having particular utility in recording the dispensing of a push-down activated aerosol medication dispenser. A non-rotative force on an outer cover is translated into a rotation of an indicator wheel relative to the outer cover by a set of flexible pawls engaged with a set of teeth. The pawls depress and thereby extend circumferentially when the applied force flexes them to effect a rotation of the teeth. Suitable means indicate the relative rotation of the teeth such as a window in the outer cover through which is visible indicia on the indicator wheel. The device may also include means to resist its operation by a child.

4 Claims, 6 Drawing Sheets

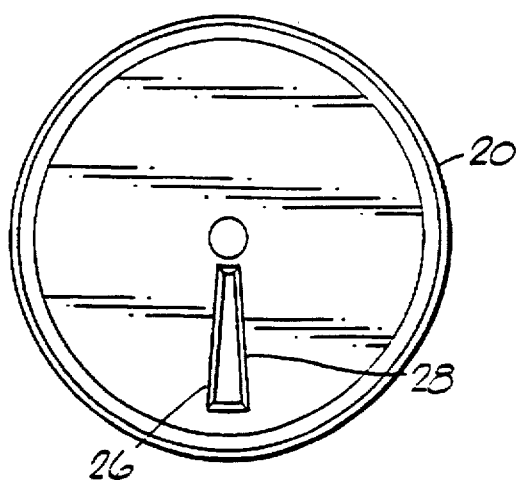
FIG.2
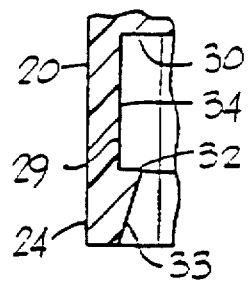
FIG.2A
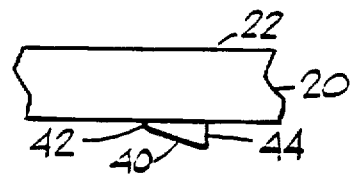
FIG.2B
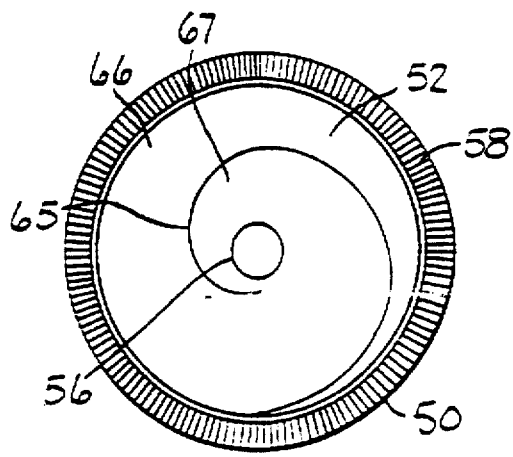
FIG.3
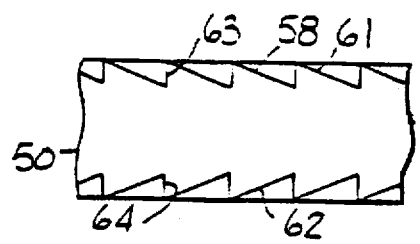
FIG.3A
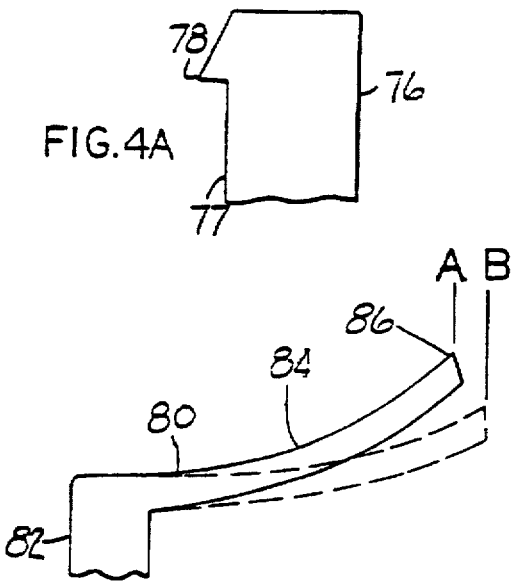
FIG.4A
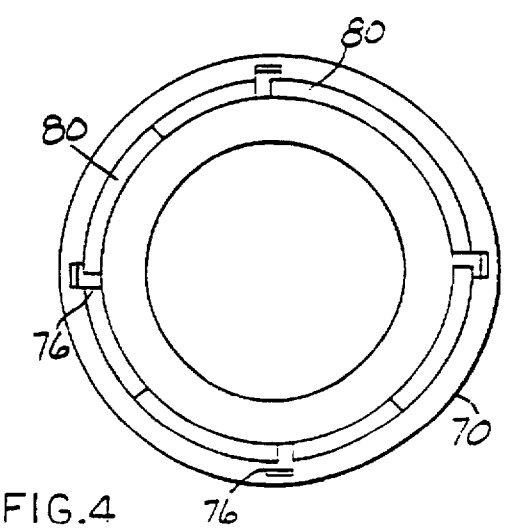
FIG.4
FIG.4B

INDICATOR DEVICE RESPONSIVE TO AXIAL FORCE

This application is a continuation of application Ser. No. 08/412,359 filed Mar. 29, 1995, now U.S. Pat. No. 5,611,444 which is a divisional of application Ser. No. 08/125,365 filed Sep. 22, 1993, which was issued as Pat. No. 5,421,482 on Jun. 6, 1995 which is a continuation-in-part of application Ser. No. 08/109,401 filed Aug. 19, 1993 issued as Pat. No. 5,299,701 on Apr. 5, 1994 which is a continuation-in-part of application Ser. No. 07/641,759 filed Jan. 17, 1991, now abandoned, which is a continuation-in-part of application Ser. No. 07/306,485 filed Feb. 3, 1989 issued as Pat. No. 5,009,338 on Apr. 23, 1992.

BACKGROUND OF THE INVENTION

The present invention relates primarily to containers, bottles, dispensers, canisters and the like and, more particularly, to an indicator mechanism to indicate the number of times the container, bottle, dispenser or canister has been opened or used. The invention can also be used for any other application in which the number of times a given activity is performed must be indicated.

In the medical field, medical drugs have a predetermined therapeutic range in which the effects of taking the drug are beneficial. Under-utilization of a drug may endanger the user with the drug's side effects without reaching levels necessary for a therapeutic action. On the other hand, over-utilization may cause side effects or toxicity to a much greater extent than any possible benefit. Thus it is critically important that a patient follow prescribed directions on medications, yet frequently patients forget whether they have taken medication and either omit doses or repeat them.

A considerable number of pill-timing schemes have been used to solve the problem of reminding a patient to take a dose of medicine or reminding the patient that the patient has already taken the dose. The most used ones involve some scheme of compartmentalization of the necessary medication, such that the pills are placed in compartments that are labeled by day, dose number or time of day, or that are serially numbered. These devices are reasonably satisfactory only if a responsible person is available and has the time and patience to fill the compartments properly.

Some medication is not in the form of a pill or capsule at all, but is instead an aerosol, such as asthma medication or other common respiratory tract medication. These medications are often packaged as a liquid in a pressurized canister which releases a measured aerosol dose into the patient's mouth or nose upon activation. Of course, such medications are not amenable to packaging in numbered compartments.

In dispensing pills of a single type, a number of window-containing bottle caps have been invented. Through the window a movable element marked with an index is visible. In only a few devices does the indicating element index in position relative to the window each time the cap is loosened, removed, replaced, and retightened. Thus, by looking at the index mark displayed through the window, a user can see where in repetitive sequence of dose he or she is. One limitation to most such devices is that they are designed to operate only with closures that disengage from a container by application of a rotative force, such as threaded or bayonet-type closures. The devices generally do not operate with closures that snap off from a container or other devices in which the container contents are accessed by the application of an axial force such as a push-actuated canister.

A serious disadvantage of prior art devices of the window indexing type is that there is no warning to the user in case the user does not turn the device far enough during the opening or closing to properly advance the window. Unless the user is alert to the index value before opening and then after closing such devices, the user will be unaware that the window failed to advance to a new index. Most users, especially the elderly who may not understand how the device operates, will not be this alert to the functioning of the device. In addition, most prior art devices fail to provide positive locking in both directions of movement; thus, the index may be moved appropriately when the device is opened or closed, but additional movement is not prevented when the device is moved in the opposite direction. This allows the index to drift, often causing failure or an incorrect reading, particularly after the device has been used over a period of time.

The device of U.S. Pat. No. 4,011,829 issued Mar. 15, 1977 to Wachsmann, et al., attempts to provide positive locking in both directions, but because of the direction of the tooth designed to prevent movement of the index upon closure, the device may not work reliably, particularly after wearing with use. Also, the device of Wachsmann does not provide space for the ratchet teeth to slide past the engagement teeth when the device is moving in a direction wherein such teeth should disengage, which may cause unreliable operation over a period of time. Another drawback of this device is its inclusion of a complicated "child proofing" feature with the indexing feature, which makes the device quite complex. Other features of this device, such as the method of providing the lost motion drive and the requirement of a post in the middle of the elements to hold the device together, also increase its complexity.

The device of U.S. Pat. No. 3,151,599 issued Oct. 6, 1964 to Livingston provides positive locking in both directions, but it does so by means of very closely spaced projections that would be difficult to manufacture economically. Furthermore, this device does not provide space for the projections to move while sliding past each other when not engaged.

The device of U.S. Pat. No. 4,666,051 issued May 19, 1987 to Trick has an indicator wheel with a serrated rim projecting above and below the plane of the wheel. The serrations engage mating serrations in upper and lower elements in order to drive the indicator mechanism. The serrations are rigid and, therefore, tend to wear excessively as they slide past one another.

The device of European Patent Application No. 87100917.2, published Jul. 27, 1987, by Schwab, has a cup-shaped exterior element that engages a frustoconical closure cap. The Schwab device is somewhat complicated in design and manufacture. The device of U.S. Pat. No. 4,220,247 issued Sep. 2, 1980 to Kramer also includes a cup-shaped exterior element which engages an inner element.

Other devices in the art include U.S. Pat. Nos. 4,511,050 by Nicol; 4,365,722 by Kramer; 4,749,093 by Trick; 4,782,966 by Thackrey; 4,753,189 by Mastman; 4,705,182 by Newel-Lewis; 4,662,520 by Griffen; 4,641,759 by Kelley; 4,634,012 by Kelley; 4,562,933 by Dennis; 4,528,933 by Allen; 4,511,050 by Nicol; 4,548,157 by Hevoyan; 4,501,370 by Kelley; 4,489,834 by Thackrey; 4,432,300 by Lyss; 4,419,016 by Zoltan; 4,405,045 by Villa-Real; 4,357,192 by Moser; 4,347,804 by Villa-Real; 4,094,408 by Ford; 3,996,879 by Walton; 3,960,713 by Carey; 3,926,326 by Grau; 3,921,568 by Fish; 3,887,099 by Gillman; 3,753,417 by Garby; 3,446,179 by Bender; 3,334,731 by Dale; 2,943,730 by Tregilgas; 2,939,597 by Greene; 2,587,147 by Guion; 498,851 by Adsit; 4,500,005 by Forrester; 3,151,599 by Livingston; 4,666,051 by Trick; 4,345,541 by Villa-Real; 4,440,306 by Van Buskirk; 2,767,680 by Lermer; 4,723,673 by Tartaglia; 2,644,452 by Brown; 4,646,936 by Frazier; 3,766,882 by Babbitt; 3,977,554 by Costa; 5,011,032 by Rollman; 5,188,251 by Kusz; 5,184,739 by Kusz; and European Patent 0 230 323 by Schwab.

It is thus apparent from a review of this art that there is a need for an improved indicator cap that operates by application of an axial rather than rotative force. Preferably, such a device should provide positive controlled movement of the index on both opening and closing of the device, while also providing an indication to the user that the index has functioned properly each time the device is used. The basic design of such a device can also be used in other applications where it is necessary to have a record of the number of times a given event occurs.

Preferably, such a cap should have a minimum of parts, should be easily manufactured and assembled using standard injection molding and assembly methods, and should be usable with ordinary containers that are not necessarily specially designed for the cap.

SUMMARY OF THE INVENTION

The present invention is an indicator device with an indicator mechanism that advances by the application of an axial force. The device thus translates axial force into the rotation of an indicator symbol carrier in relation to a pointer or window. The device is particularly suited for use with aerosol-type medications which are administered by applying an axial force to a canister, or for use with medications that are kept in a container with a snap closure.

The advancement mechanism utilizes the axial force to move two or more elements axially in relation to one another, and this relative axial movement is transformed into a rotation of an element in relation to another element by an indicator mechanism. The invention in a preferred embodiment includes an outer cover having a top and a depending skirt attached to the top; and a driver (sometimes referred to as a retainer herein) which nests in the skirt of the outer cover. The invention also includes a rotational mechanism which may be separate from the outer cover and driver. In the preferred embodiment, there is an indicator wheel which nests in the skirt of the outer cover between the driver and the outer cover. The driver has several lugs which mate with several notches in the radially inner surface of the outer cover to hold the assembly together. The notches allow a measure of movement of the lugs in the axial direction, so that there is some play between the driver and the outer cover in the axial direction. The indicator wheel has a set of teeth on one side which engage a set of flexible angled pawls on the driver, and a set of teeth on the other side which engage a set of outer cover teeth on the other side. When an axial force is applied urging the outer cover and driver together, the outer cover and driver move toward one another slightly as the driver lugs move axially in the outer cover notches. The angled pawls in the driver flex toward the driver or "flatten out", which causes the driver pawl ends to shift slightly around the axis of the driver. This shift of the driver pawl ends, which are engaged with the indicator wheel teeth, drives the indicator wheel so as to rotate the indicator wheel relative to the driver. The rotation of the indicator wheel relative to the driver also results in rotation of the indicator wheel relative to the outer cover, since the engagement of the driver lugs with the outer cover notches ensure that the driver and outer cover are rotatively fixed.

The side of the indicator wheel that is against the outer cover has indicia which are viewable through a window in the outer cover to indicate the progressive rotation of the indicator wheel as the axial force urging the outer cover and driver together is repeatedly applied. The indicia may be in the form of a sequence of numbers or, in the preferred embodiment, a spiral line or pattern which produces a "gauge" when viewed through the outer cover window which appears to decline as the device is used repeatedly so as to progressively rotate the indicator wheel in relation to the outer cover. In this way, a record is kept of the total number of doses administered so that the user has some indication of whether an aerosol medication canister, for example, is being used up. Alternatively, the indicia on the indicator wheel may be numbers or symbols that record or limit the number of doses in a day, or words such as "empty" or "full".

When the axial force urging the outer cover and driver together is released, the driver pawls push the outer cover and driver apart. This allows the driver pawl ends to flex away from the driver and rotatively in the opposite rotative direction from the direction of rotation when the axial force was applied. This opposite rotative movement of the driver pawl ends causes the driver pawl ends to pass over a tooth of the indicator wheel, thereby "cocking" the mechanism for the next time an axial force is applied. This cocking and driving action causes the indicator wheel to advance by one tooth with each separate application of an axial force.

As explained in the preceding paragraph, the device is accomplished by the rotative movement of the driver pawl ends in relation to the indicator wheel teeth, so that the driver pawl ends pass over one of the indicator wheel teeth. During this cocking step, the indicator wheel is prevented from rotating by the engagement of the teeth that are on the opposite side of the indicator wheel with the teeth in the outer cover. Thus, the outer cover and driver do not rotate in relation to one another, and the indicator wheel rotates in relation to both a single direction but not in the opposite direction. The engagement of the driver pawls with the teeth on one side of the indicator wheel produces the rotation of the indicator wheel in that single direction, while the engagement of the outer cover teeth with the teeth on the opposite side of the indicator wheel prevents rotation of the indicator wheel in the opposite direction.

The invention thus provides a system to indicate the administration of medication through a medication container which is accessed by the application of an axial force, such as a canister-contained aerosol, or a snap closure or a "push-and-turn" type child-resistant closure on a vial for pills or capsules. In the case of a canister, the driver may be attached directly to the canister end with an adhesive or double-sided tape, or the driver may include a skirt which press-fits over the canister end, or the device may be attached to the canister or to a canister dispenser by other suitable means. The device may also be used in any other application in which an indication of the occurrence of an event is desired. The device is incapable of advancing without applying the requisite axial force which accesses the medication, but it advances in precise and predetermined increments when that axial force is applied.

An additional advantage to the invention is that it produces audible "clicks" to confirm that it is operating properly. When the axial force is applied to access the medication and thereby advance the indicator wheel, the indicator wheel teeth on the side adjacent the outer cover pass over the teeth of the outer cover to produce a "click" or "clicks" to confirm the advancement of the indicator wheel. When the axial force is released, the driver pawls pass over the teeth of the indicator wheel on the side adjacent the driver to produce a second "click" or "clicks" to confirm the proper "cocking" of the mechanism.

Other advantages of the invention include its simplicity of manufacture, assembly and operation, and its reliability.

BRIEF DESCRIPTION OF THE DRAWINGS

FIG. 2 is a top view of the outer cover of the invention.

FIG. 2A is a side sectional view of a portion of the outer cover of the invention.

FIG. 2B is a side sectional view of a portion of the outer cover of the invention.

FIG. 3 is a top view of the indicator wheel of the invention.

FIG. 3A is a side sectional view of a portion of the indicator wheel of the invention.

FIG. 4 is a top view of the driver of the invention.

FIG. 4A is a side sectional view of a portion of the driver of the invention.

FIG. 4B is a side sectional view of a portion of the driver of the invention.

DETAILED DESCRIPTION OF THE INVENTION

Figure 1:
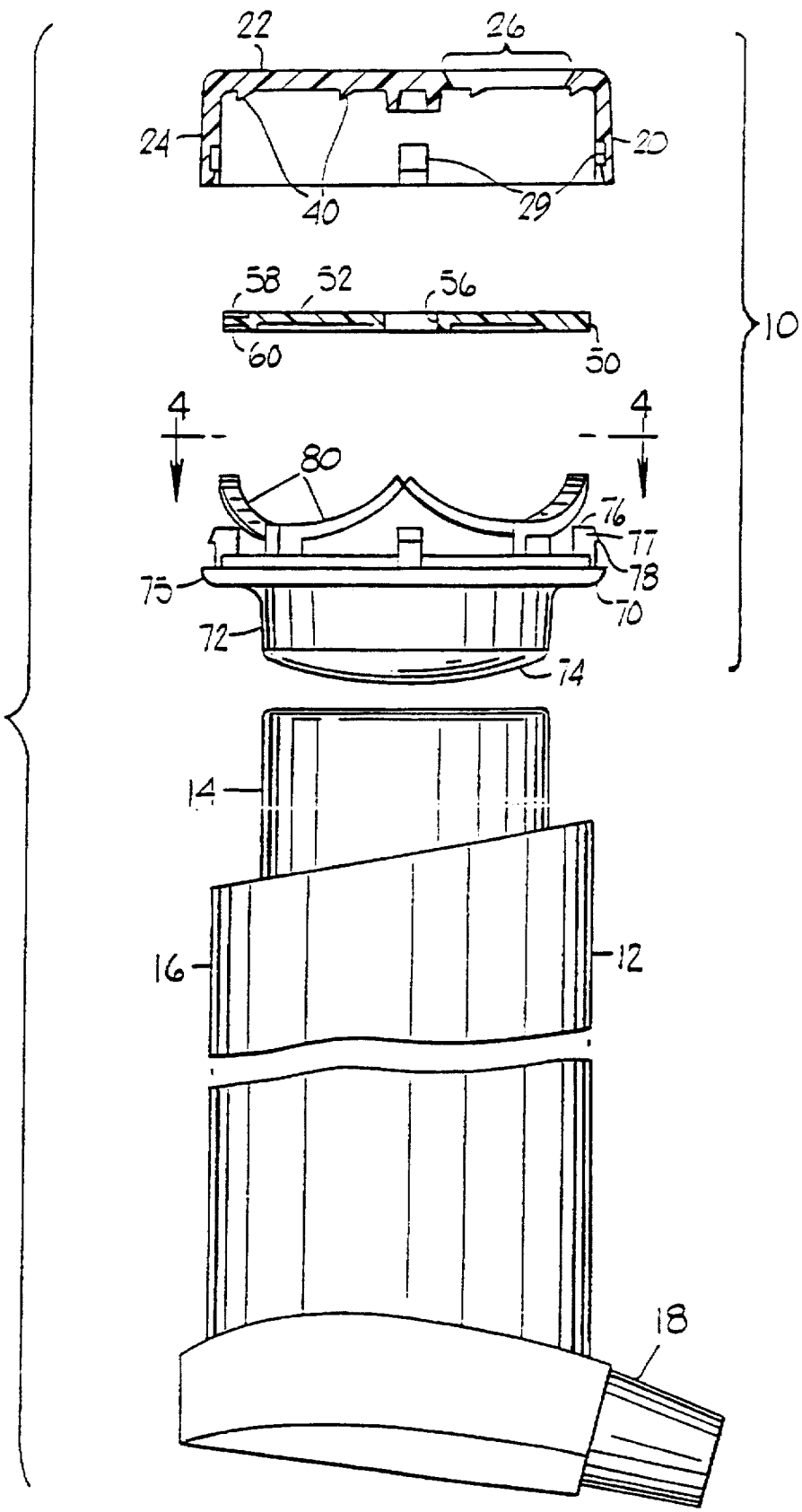
FIG. 1 is an exploded elevational view of the present invention with a canister and canister case.

An exploded elevational view of the invention 10 together with an ordinary canister aerosol medication dispenser 12 is shown in FIG. 1. The dispenser 12 includes a canister 14 which is housed in a canister case 16. Aerosol medication is dispensed from the canister 14 by grasping the canister case 16 and applying a force urging the canister 14 toward the canister case 16 to actuate a valve (not shown) in the canister 14, to release a measured dose of medication from the canister 14 and out the canister case outlet 18. The medication administered in this manner is typically respiratory tract medication such as asthma medication, and so the canister case outlet 18 is placed into the patient's mouth as the patient inhales. The system is quite reliable and simple to operate, and so it is often operated by the patient himself without the aid of a health care professional. Aerosol medication systems such as this are well known in the art, and will not be described in detail here.

The invention 10 includes three main elements in the preferred embodiment of FIG. 1: an outer cover 20, an indicator wheel 50, and a driver 70. (While the invention in a preferred embodiment is mechanical, it should be recognized that the mechanism could be replaced with a simple electronic button attachable to the canister which actuates upon applying the valve-actuating force.) The three elements are described in detail with reference to FIG. 1, as well as reference to FIGS. 2, 2A and 2B for the outer cover 20, FIGS. 3 and 3A for the indicator wheel, and FIGS. 4, 4A and 4B for the driver, and then the operation of the device is described with reference to the previously mentioned figures.

The outer cover includes a top 22 and an axially depending skirt 24 extending from the top. The axially depending skirt may flare radially outward slightly as it extends downward, in the manner shown, to facilitate the assembly of the device. Through the top 22 is a window 26. As better shown in FIGS. 2 and 2A, the window 26 extends radially from near the center of the top to near the perimeter, and is of a width sufficient to allow the viewing of the indicia on the indicator wheel 50 in the manner described below. The edges 28 of the window 26 may be beveled in the manner shown to improve the aesthetics of the device, or to improve the tactile aspects of the window for use with raised or depressed indicia (or braille symbols) on the indicator wheel that can be sensed in the dark or by the sight-impaired.

Spaced around the radially inner surface of the depending skirt 24 are a set of notches 29, which are better shown in the sectional view detail of FIG. 2A. Each notch 29 includes an upper wall 30 and a flat portion 34. A retainer 32 defines the lower end of the flat portion 34, and a bevelled portion 33 extends from the retainer to the bottom of the depending skirt 24. The circumferential width of the notch is just enough to receive the lugs 76 of the driver 70 described below without allowing any significant circumferential play between the notches 29 and those lugs 76. The lugs and notches of the preferred embodiment may be replaced with a slot and groove or a hole and post or any other arrangement allowing axial movement of the outer cover relative to the retainer.

In the center of the bottom surface of the top portion 22 of the outer cover 20 is an axially extending hub 36 which mates with a central hole 56 of the indicator wheel 50 in the manner described below. Also on the bottom surface of the top portion 22, around the periphery which meets the depending skirt 24, are a set of outer cover teeth 40 which engage the indicator wheel teeth 58 in the manner described below. The outer cover teeth 40, better shown in the sectional detail of FIG. 2B, include a ramp 42 on one side and a face 44 on the other side which engage the indicator wheel teeth 58 to produce a ratchet effect between the outer cover 20 and the indicator wheel 50 in the manner described below.

The indicator wheel 50 is a disk-shaped element having an upper surface 52, a lower surface 54 and a hole 56 through the middle. The diameter of the disk-shaped indicator wheel 50 is such that it nests into the outer cover 20. The upper surface 52 includes a set of indicator wheel upper teeth 58 around the periphery of the upper surface 42 as better shown in FIGS. 3 and 3A, and the lower surface 54 includes a set of indicator wheel lower teeth 60 around the periphery of the lower surface 54.

The indicator wheel teeth 58 and 60 are shown best in the elevation detail of FIG. 3A. Both the teeth 58 on the upper surface 52 and the teeth 60 on the lower surface 54 include a ramp portion 61 and 62, respectively, and a face portion 63 and 64, respectively. As explained in more detail below, the ramp portion 42 of the outer cover teeth 40 and the pawl ends 86 of the driver pawls 80 ride over the ramp portions 61 and 62 of the indicator wheel teeth 58 and 60 to allow rotation of the indicator wheel 50 in one direction in relation to the outer cover 20 and driver 70, while the pawl ends 86 of the driver pawls 80 and the faces 44 of the outer cover teeth 40 engage the faces 63 and 64 of the indicator wheel teeth 58 and 60 to prevent rotation of the indicator wheel 50 in the opposite direction in relation to the outer cover 20 and driver 70.

On the upper surface 52 of the indicator wheel 50 is a line 65 which extends spirally from near the central hole 56 to near the radially inner edge of the upper teeth 58, in the manner shown in FIG. 3. Preferably, the surface 66 on one side of the line is one color and the surface 67 on the other side of the line is a different color; for example, the surface on one side can be red and the surface on the other side may be white. As the line 65 with the differently colored surfaces 66 and 67 are presented for viewing through the window 26 of the outer cover 20 when the device is assembled, a kind of gauge results, as described in more detail below. The differing colors can be accomplished with the use of printing, painting, adhesive materials or other methods known in the art.

The driver 70 includes a circular base 72 with a bottom 74 configured to mate with the canister 14 of the canister aerosol medication dispenser 12. Such canisters typically have a concave end, and so the driver bottom on the preferred embodiment is convex as shown in FIG. 1 to mate with the canister concave end. The driver 70 is attached to the canister using a suitable driver mount such as a double-sided adhesive pad. The diameter of the base 72 is preferably about the same as the diameter of the canister 14, so that the base 72 can be pushed into the canister case 16 if necessary to actuate the canister valve. Other mounts are feasible such as a clamp or a buckle, or mounts that make the driver integral with the canister or mounts that make the device resistant to operation by a child. One such other mount—a press-fit mount—is described in connection with the alternate embodiment described below.

Above the base 72 on the driver 70 is an annular ring 75 which holds several elements. The annular ring 75 is preferably of a diameter greater than the diameter of the base 72 and canister 14. This ensures that the canister end is not accessible to the user, so that the user must access the medication by applying a force to the device 10 to advance the indicator wheel 50 rather than by applying the force directly to the canister and thereby bypassing the device 10.

The annular ring 75 has a set of lugs 76 protruding upwardly. As better shown in the elevational detail of FIG. 4A, each lug 76 has a lug body 77, and a lug point 78 which engages the notches 29 of the outer cover 29 in the manner described below. The lug body 77 is somewhat flexible, so that it can flex radially inward as the lugs 76 pass over the bevelled portion 33 of the outer cover notches 28 when the driver 70 is assembled into the outer cover 20. The lug body 77 and the lug point 78 are dimensioned such that there is some axial play between the driver 70 and the outer cover 20; that is, the lugs 76 may extend all the way into the notches 28 so that the top of the lug body 77 is against the top wall 30 (see FIG. 2A) of the notch 29 while the outer cover 20 and driver 70 are positioned closely together, or the lugs 76 may be partially withdrawn from the notches 28 so that the lug point 78 is against the notch retainer 32 while the outer cover 20 and driver 70 are positioned further apart.

Also extending upward from the annular ring 75 of the driver 70 is a set of driver pawls 80. Each driver pawl 80 includes a pawl base 82 and a curved flexible pawl body 84 which extends circumferentially and upwardly to terminate in a pawl end 86, all as better shown in FIG. 4B. The pawl end 86 engages the indicator wheel lower teeth 60 in a ratcheting manner whereby the pawl end passes over the ramp portion 62 of the indicator wheel lower teeth 60.

An important aspect of this embodiment of the invention is that the flexing of the pawls 80 produces an elongation of the circumferential dimension of the pawl, as shown in the exaggerated depiction of FIG. 4B. The pawl in solid lines is relatively unflexed, while the pawl in dashed lines is relatively flexed. The unflexed position exists when the outer cover 20 and driver 70 are positioned apart, as when the driver lugs 76 are relatively withdrawn from the outer cover notches 29. In that position, the pawl end 86 is at circumferential position "A". The flexed position exists when the outer cover 20 and driver 70 are positioned together, as when the driver lugs 76 are fully positioned into the outer cover notches 29 against the notch top wall 30. In that position, the pawl end 86 is flexed downward by bending about the pawl base 82 and along the pawl body 84. The bending results in a shift in the pawl end 86 to position B, which is circumferentially spaced apart from position A. Because the pawl end 86 is engaged with the face 64 of the indicator wheel lower teeth 60 when the pawl 80 is in the relatively unflexed position corresponding to pawl end position A, the flexing of the pawl by the forcing together of the outer cover 20 and driver 70 and consequent shifting of the pawl end to position B forces the indicator wheel 50 to rotate the distance between position A and position B in relation to the driver 70. When the force between the outer cover 20 and driver 70 is removed, the pawl unflexes to drive apart the outer cover 20 and driver 70. This unflexing allows the pawl end 86 to return to position A. The indicator wheel 50, however, does not rotate back to the earlier position where it was before the flexing because the pawl end is free to ride over the ramp portion 62 of the indicator wheel lower teeth 60. Moreover, the indicator wheel is prevented from rotating back to that earlier position by the one-way ratchet effect of the outer cover teeth 40 engaged with the indicator wheel upper teeth 58 as described below.

The device 10 is preferably made by high-speed processes such as plastic injection molding. Once the molding of the three main pieces is completed, the pieces are assembled by hand or by automated assembly machines by nesting the indicator wheel 50 into the outer cover 20 and then forcing the driver lugs 76 into the outer cover notches 29, so that the driver lugs 76 are retained in the outer cover notches 29 by the notch retainer 32 bearing against the lug points 78. When the lugs 76 are positioned in the notches 29, the driver pawls 80 are slightly flexed to provide a biasing force against the indicator wheel lower teeth 60. This biasing force holds the indicator wheel 50 against the outer cover 20 to maintain engagement of the indicator wheel upper teeth 58 with the outer cover teeth 40, to maintain engagement of the pawl ends 84 with the indicator wheel lower teeth 60, and to position the outer cover 20 and driver 70 in their relatively apart position and ready for use.

After assembly, the device 10 is attached to a medicine container such as the canister 14 shown in FIG. 1 or some other canister, vial, bottle or container, by use of double-sided adhesive tape or other suitable attachment means. The attachment means may include child-resistant elements so that the device is resistant to operation by a child.

The device is operated by applying an axial force urging the outer cover 20 toward the canister 14. The application of such force produces several kinds of movements, which may occur simultaneously with one another or in sequence in any order. One kind of movement is the actuation of the valve of the canister 14 to release a measured amount of aerosol medication from the canister and out the outlet 18 of the canister case 16. The other kind of movement produced by the application of an axial force urging the outer cover 20 toward the canister 14 is movement within the device 10. The axial force on the outer cover moves the outer cover toward the driver 70, which causes the driver lugs 76 to shift upward in the outer cover notches 29 until the tops of the driver lugs 76 are against the upper wall 30 of the outer cover notches 29.

This second kind of movement—the moving together of the outer cover 20 and driver 70 caused by the axial force applied to the outer cover—also depresses the driver pawls 80, the ends 86 of which are engaged by the indicator wheel lower teeth 60. This depression—or flexing—of the driver pawls, as explained above, results in a circumferential lengthening of the pawls due to the pivoting of the pawl body 84 about the pawl base 82 and along the pawl body. FIG. 4B shows an exaggerated depiction of this circumferential lengthening of the pawl 80 from the unflexed circumferential position A (where the pawl 80 is shown in solid line) to the flexed circumferential position B (where the pawl 80 is shown in dashed lines). Because the pawl end 86 is engaged with the indicator wheel lower teeth 60, this circumferential lengthening of the driver pawls 80 drives the indicator wheel through the incremental circumferential distance of position A to position B, thus producing a rotation of the indicator wheel 50 relative to the driver 70. It can be appreciated that, because the pawls are flexible, this flexing may also produce flattening of the curvature in the pawls which also tends to lengthen them. The indicator wheel lower teeth 60 and driver pawls 80 are dimensioned such that this incremental circumferential shift is the length of a single tooth of the indicator wheel lower teeth 60.

It is noted that the rotation of the indicator wheel 50 does not translate into any rotation of the outer cover 20, because the outer cover 20 is rotationally fixed in relation to the driver 80 by the engagement of the driver lugs 76 in the outer cover notches 29.

Thus, the overall effect on the device 10 of applying an axial force urging the outer cover 20 toward the driver 70 is, one, the outer cover 20 shifts toward the driver 70 as the driver lugs 76 move upward in the outer cover notches 29 and, two, the indicator wheel 50 rotates counterclockwise in relation to the outer cover 20 and driver 70. This counterclockwise rotation of the indicator wheel 50 in relation to the outer cover 20 shifts to the window 26 of the outer cover 20 a new portion of the indicator wheel upper surface 52. With reference to FIG. 3, that new portion of the indicator wheel upper surface 52 is slightly clockwise from the upper surface 52 that was previously at the window 26. Because the upper surface 52 includes a spiral line or pattern as explained above and as shown in FIG. 3, which appears as a "gauge" when viewed through the widow 26, the progressive rotational shift of the upper portion 52 viewable through the window has the effect of creating a declining or ascending line in the window. Thus, the repeated application of an axial force to the outer cover 20 gradually rotates the indicator wheel 50 to result in the appearance of a declining or ascending "gauge" in the window 26.

Referring again to the preferred embodiment of FIGS. 1–3B and 4–4B, the release of the axial force urging the outer cover 20 toward the canister 14, allows the flexed driver pawls 80 to unflex toward their natural relaxed position. This unflexing of the driver pawls forces the outer cover 20 and indicator wheel 50 away from the driver 80, so that the driver lugs 76 move downward in the outer cover notches 29 until the lug points 78 are stopped by the notch retainers 32 (see FIGS. 4A and 2A). The unflexing of the driver pawls 80 causes the pawl ends 86 to shift back to circumferential position A from circumferential position B. However, this circumferential shifting of the pawl ends 86 as the pawls 80 unflex does not produce any rotation of the indicator wheel 50. This is because the indicator wheel lower teeth 60 have a ramp 62 on one side and a face 64 on the other side (see FIG. 3A) to produce a one-way ratchet effect. The flexing of the pawls 80 when an axial force is applied urging the outer cover 20 toward the drawer 80 causes the pawl ends 86 to shift circumferentially while engaged with the face 64 to drive the indicator wheel 50 through an incremental rotational movement. However, the release of that force and the consequential unflexing of the pawls 80 and circumferential shifting back to the pawl ends 86 does not rotate the indicator wheel 50 in the opposite direction, because the pawl ends 86 simply ride over the ramp portions 62 of the indicator wheel lower teeth 60.

This rotation of the indicator wheel 50 in relation to both the outer cover 20 and driver 80 has one other important effect. As the indicator wheel 50 rotates in relation to the outer cover 20, the outer cover teeth 40 ride over the indicator wheel upper teeth 58. More specifically, the ramp portions 42 of the outer cover teeth 40 ride over the ramp portion 61 of the indicator wheel upper teeth 58. The outer cover teeth 40 and indicator wheel upper teeth 58 are dimensioned such that the circumferential shift of the pawl ends 86 from position A to position B (see FIG. 4B) in the course of one cycle of applying an axial force urging the outer cover 20 toward the driver 80, causes the indicator wheel upper teeth 58 to shift one tooth in relation to the outer cover teeth 58. When the outer cover teeth 40 drop over the face 63 of the indicator wheel upper teeth 58 as this one-tooth shift occurs, an audible "click" results. This "click" confirms to the user that the indicator wheel has properly advanced.

The indicator wheel lower teeth 60, as mentioned above, are dimensioned such that the circumferential movement of the pawl ends 86 produced by applying or releasing an axial force to the outer cover 20, corresponds to one tooth. Therefore, the circumferential shift in the pawl ends 86 resulting from releasing the axial force on the outer cover 20, is equal to one tooth. The passing of the driver pawls 86 over the ramp portion 62 and over the face 64 of a tooth of the indicator wheel lower teeth 60, produces another audible "click". This "click", unlike the first "click" previously described, does not confirm any advancement of the indicator wheel 50, since the indicator wheel 50 does not advance at that time; rather, this "click" confirms that the driver pawls 80 have advanced by one tooth in the indicator wheel lower teeth 60, so that the driver pawls 80 will advance the indicator wheel 50 the next time an axial force is applied to the outer cover 20 to flex the driver pawls 86. Although the description above indicates that the passing of the driver pawls over a set of teeth produces a "click", it should be reorganized that actually there may be a set of several "clicks" of the four pawls to not pass over their respective teeth exactly simultaneously due to inexactness in the dimensions of the elements. Instead, there may be as many as four closely spaced "clicks".

When the axial force is released from the outer cover 20 so that the driver pawls are permitted to unflex, the indicator wheel 50 is positively prevented from rotating back to its previous position before it was last advanced, by the engagement of the indicator wheel upper teeth 58 with the outer cover teeth 40. As described above, those sets of teeth 58 and 40 act as a one-way ratchet; rotation of the indicator wheel 50 is allowed in one direction as the ramp portion 42 of the outer cover teeth 40 ride over the ramp portion 61 of the indicator wheel upper teeth 58, but rotation of the indicator wheel 50 is prevented in the other direction by the engagement of the face 44 of the outer cover teeth 40 with the face 63 of the indicator wheel upper teeth 58.

The device 10 has been explained above in a preferred embodiment having teeth and pawls of certain elements and in certain positions. It will be apparent to those skilled in the art that some of these arrangements may be revised or reversed without departing from the scope or spirit of the invention. For example, without limitation, the teeth and pawls could be designed so that the indicator wheel advances when the force on the outer cover is released so that the outer cover and driver separate rather than when a force is applied so that the outer cover and driver come together; the pawls could be on the indicator wheel and the engaged teeth on the driver rather than the other way around; the outer cover teeth and indicator wheel upper teeth could be reversed; and the pawls could be between the outer cover and the indicator wheel rather than between the indicator wheel and driver so that the pawls are positioned on the indicator wheel upper surface or the outer cover lower surface. It will also be apparent that the pawls and teeth on the various elements could be positioned on the outer circumference extending radially outward (or the inner circumference extending radially inward in the case of a disk having a center hole), rather than on the upper or lower surfaces extending upward or downward.

It should also be apparent from studying the drawings that the radial position of the pawls 80 is important in producing the desired amount of rotation of the indicator wheel. If the pawls are positioned toward the radially outer edge of the device, as shown in the figures, the circumferential shift in the pawl ends 86 produced by the flexing of the pawls 80 will result in a relatively small rotation of the indicator wheel. On the other hand, if the pawls are positioned to the center of the device, the same amount of circumferential shift in the pawl ends 86 produced by the flexing of the pawls 80 will result in a relatively large rotation of the indicator wheel. Also, the degree of advancement of the indicator wheel is dependent on the distance that the outer cover moves toward and away from the retainer. This also relates to the length of the pawls, since a set of long pawls used for long distances between the outer cover and retainer will produce a greater advancement while a set of short pawls will produce a lesser advancement. Of course, the degree of advancement is also dependent on the curvature of the pawls and the geometry of the arrangement.

As previously mentioned, the upper surface 56 of the indicator wheel 50 may have indicia other than a spiral line to produce a declining or ascending line when viewed through the window 26, depending on the desired use of the device. For example, if it is desired to use the device to ensure that the patient takes a prescribed dose of medicine in prescribed time periods, and no more and no less, then the indicia may include abbreviations of the days of the week (such as Sa, Su, M, Tu, W, etc. for once a day medication or Sa1, Sa2, Su1, Su2, M1, M2, etc. for twice a day medication) arranged in a circle around the top surface 56. The teeth and pawls of the device are then dimensioned and configured such that each advancement of the indicator wheel 50 produced by applying a force urging the outer cover 20 toward the driver 70, advances one symbol under the indicator wheel. Thus the indicia visible through the window 26 successively advances through Sa, Su, M, Tu, W, etc. or Sa1, Sa2, Su1, Su2, M1, M2, etc. as the device is repeatedly operated. As another example, the indicator wheel 50 upper surface 56 may have a spiral line as indicia, but the spiral may be of such a configuration, and the teeth and pawls of the device of such a configuration and dimension, that the gauge produced by the viewing of a portion of the spiral line through the window moves through its entire range based not on the contents of the medication canister but on the allowable dosage in a day or in some other chosen time period. For example, if the medication is prescribed for discretionary as-needed administration to the patient, but not more than five times a day, then the gauge would go through its entire range with five doses dispensed. Thus, by a glance at the window, the user can determine how close he or she is to the maximum daily dose. At the outset of a new day, the gauge is reset.

The spiral line on the top of the indicator wheel 50 may go through approximately 360° as shown in FIG. 3 or any angle more or less than that. If the spiral line goes through less than 360°, then of course, the gauge goes through its entire range in something less than a full revolution of the indicator wheel relative to the outer cover. Thus, it would be necessary in that instance to reset the gauge to the starting position when the gauge indicates that the canister is empty and the next canister is started. If the spiral line is more than 360°, then two or more portions of the line may be visible at the same time through the window, and the user may have some difficulty in ascertaining which of the line portions is the correct one corresponding to the amount of medication remaining in the canister.

On the other hand, a spiral line that goes through more than 360° has the advantage of allowing for a gauge that "moves" in lesser increments than with a spiral line of 360° or less. This may be important because there is a practical limit to the number of teeth that can e engaged with the pawls of the device. While it is feasible to mold about 240 teeth onto the indicator wheel for engagement with the driver pawls, which corresponds to the number of doses in common canister-contained aerosol medication such as asthma medication, it is not readily feasible to mold many more than 240 teeth onto a device having a convenient size. Therefore, common canister-contained medication that contains about 240 doses can be used with a device having 240 teeth so that each time the medication is administered, the indicator wheel rotates 1/240 of a full circle and the gauge declines from full to empty in one revolution of the indicator wheel. But if the canister contains, for example, 500 doses, then it is difficult to mold the necessary 500 teeth to produce a gauge that declines from full to empty in one revolution of the indicator wheel.

Figure 3B:
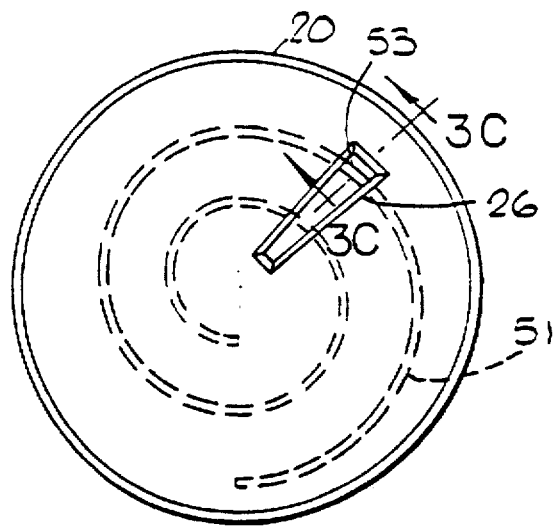
FIG. 3B is a top view of an alternate embodiment of the invention.
Figure 3C:
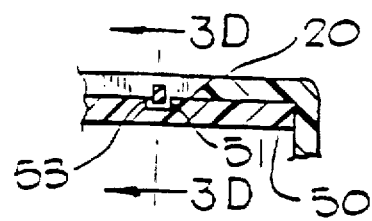
FIG. 3C is a side sectional view of an alternate embodiment of the invention, taken along line 3C—3C of FIG. 3B.
Figure 3D:
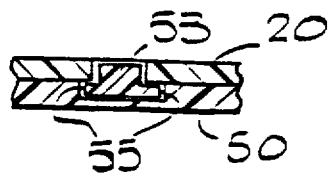
FIG. 3D is a side sectional view of an alternate embodiment of the invention, taken along line 3D—3D of FIG. 3C.

An approach to this problem is as shown in FIG. 3B which is a top view of the invention. The indicator wheel 50 includes a spiral groove 51 which extends more than 360° (720° in the embodiment of FIG. 3B). The spiral groove 51 receives a small marker 53, better shown in FIG. 3C taken along line 3C—3C of FIG. 3B and FIG. 3D taken along line 3D—3D of FIG. 3C. The marker 53 is a small key that slidable fits into the spiral groove at the window 26. It is restrained from falling out of the spiral groove and the window 26 by a pair of ears 55 which extend along the spiral groove 51 under the outer cover 20. Thus, when the indicator wheel 50 rotates relative to the outer cover 20, the marker 53 slides in the spiral groove 51 and stays visible in the window 26. As the marker 53 slides in the spiral groove 51, it moves radially toward the center or perimeter of the outer cover 20, thereby acting as a gauge. Of course, the marker may be painted a distinctive color to aid in distinguishing it from the background of the indicator wheel 50 visible through the window 26. Also, the tabs of the marker may be flexible so that they can deform to allow the tab to be displaced back to the start position after reaching the end position.

It should also be appreciated that the spiral line or groove described above need not be a true geometric spiral. For example, the line or groove can be configured to move rapidly toward the center when it is near the periphery, and then slowly when it is near the center of the indicator wheel 50, so that the user has ample warning when the canister is running low.

Figure 7:
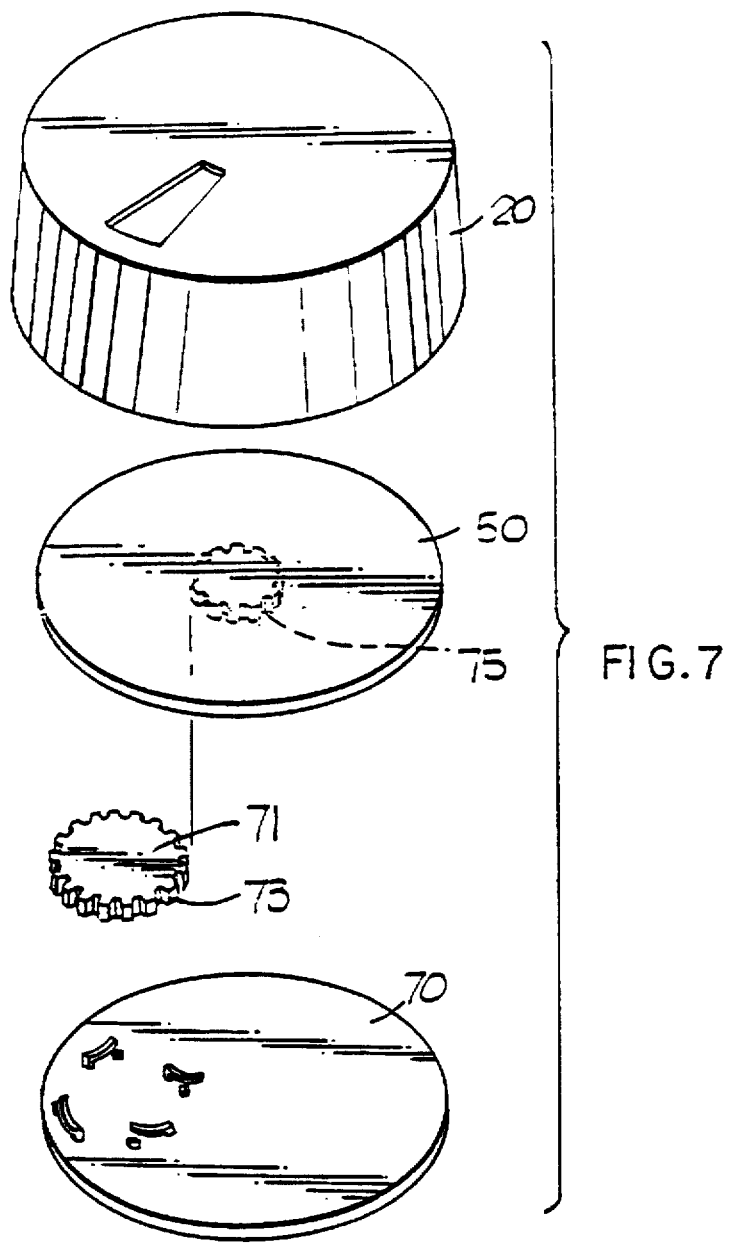
FIG. 7 is an exploded perspective view of an alternate embodiment of the present invention.

An opposite approach is shown in the exploded perspective view of FIG. 7 in which some details are omitted for clarity. This embodiment includes the already-discussed elements of a driver 70, an indicator wheel 50 and an outer cover 20. However, the driver pawls 73 are arranged in a small circle on one side of the driver 70. Rather than bearing directly against a set of teeth on the indicator wheel 50, the pawls bear against a set of teeth on the bottom of a reduction wheel 71. The reduction wheel 71 has the driver pawls 73 around its perimeter which engage a toothed hub 75 on the indicator wheel 50. It can be appreciated that the rotation of the reduction wheel 71 is increased when transferred to the indicator wheel 50, by the gear ratio of those two wheels. If, for example, the gear ratio is 10 to 1 and there are 200 teeth on the bottom of the reduction wheel 71 which are engaged one at a time by the pawls on the driver 70, then it will take 20 advances to turn the indicator wheel a complete revolution relative to the outer cover 20.

It should also be appreciated that the window of the preferred embodiment could be replaced with a hole in the outer cover and a hub in the indicator wheel extending into the hole so that it is visible through the outer cover. Then, the hub has an arrow and the outer cover has a set of symbols arranged in a circle, or vis a versa. Each time the indicator wheel rotates relative to the outer cover, the arrow points to a new symbol.

Figure 3E:
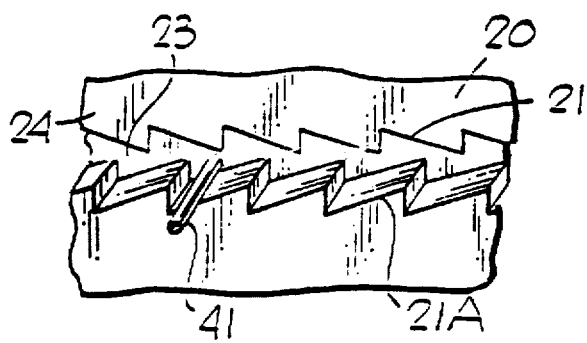
FIG. 3E is a partial perspective view of an alternate embodiment of a mechanism to advance the indicator wheel relative to the outer cover of the present invention.
Figure 3F:
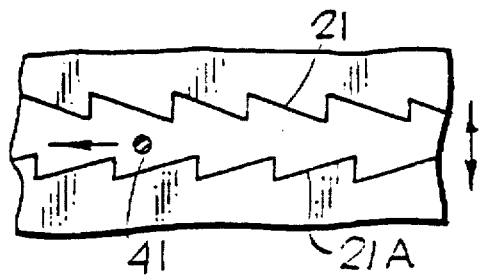
FIG. 3F is a partial side elevation view of the elements shown in FIG. 3E.

It is possible to use other mechanisms to translate the axial force applied to the outer cover to a rotation of the indicator wheel relative to the outer cover, such as the mechanisms shown in FIGS. 3E and 3F. FIG. 3E shows a partial perspective view of the inside of the depending skirt 24 of the outer cover 20, looking radially outward. The inside of the depending skirt 24 includes a radially extending groove 23 which goes completely around the depending skit 24, although only a portion of the groove 23 and the depending skirt 24 are shown in the drawing of FIG. 3E for clarity. The top of the groove 23 is bounded by an upper set of teeth 21 and a lower set of teeth 21A. Disposed in the groove 23 between the upper set of teeth 21 and the lower set of teeth 21A is at least one engaging tab 41 which extends radially outward from the indicator wheel (not shown for clarity) into the groove 23. The engaging tab may be of any suitable cross-section, and the one in FIGS. 3E and 3F is of a circular cross-section.

In operation, the force applied to the top of the outer cover 20 to release medication, serves to move the outer cover 20 and the indicator wheel 50 together. This relative movement of the outer cover 20 and indicator wheel 50 together causes the engager tab 41 of the indicator wheel to ride along a ramp of a tooth of the upper set of teeth 21. Because the ramp is at an incline, the engager tab 41 rides down the ramp, which drives the indicator wheel 50 circumferentially to result in a rotation of the indicator wheel 50 relative to the outer cover 20. When the engager tab 41 is all the way to the bottom of the ramp, the outer cover 20 and indicator wheel 50 can move no closer together and the indicator wheel 50 cannot rotate any further relative to the outer cover. Medication has now been dispensed, and the force on the outer cover is released. The outer cover 20 then moves away from the indicator wheel 50 (which movement may be assisted by a flexible pawl or other spring-like element disposed between the outer cover 20 and the indicator wheel 50). The engager tab 41 moves across the width of the groove 23 and engages a ramp of a tooth of the lower set of teeth 21A. That ramp then serves to drive the engager tab 41 another increment circumferentially to effect another incremental rotation of the indicator wheel 50 relative to the outer cover 20. Thus, it can be seen that the indicator wheel 50 rotates relative to the outer cover 20 incrementally as a force in applied to the outer cover 20 and then incrementally again as the force is released from the outer cover 20. By arranging the indicia on the indicator wheel and dimensioning the teeth 21 and 21A appropriately, the device thus counts in a discernable fashion the dispensing of medication.

Figure 3G:
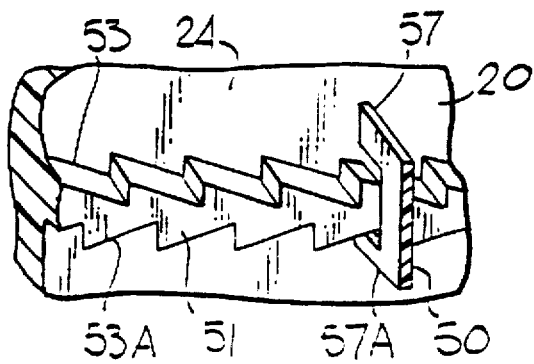
FIG. 3G is a partial perspective view of another alternate embodiment of a mechanism to advance the indicator wheel relative to the outer cover of the present invention.
Figure 3H:
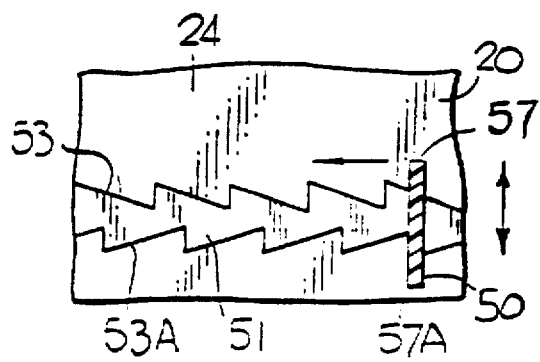
FIG. 3H is a side elevational view of the elements of FIG. 3G.

Yet another mechanism to translate the axial force applied to the outer cover to a rotation of the indicator wheel relative to the outer cover, is shown in FIGS. 3G and 3H. The general concept of this mechanism is similar to that shown in FIGS. 3E and 3F, in that it relies upon teeth having an inclined ramp and an engaging device which is driven circumferentially by the ramp. FIG. 3G is a partial perspective view of the inside of the depending skirt 24 of the outer cover 20, looking radially outward. The inside surface of the depending skirt includes a rib 51 extending radially inward. For clarity, only a portion of the rib 51 and the depending skirt 24 are shown, although it will be appreciated that the rib extends all the way around the depending skirt 24. The upper side of the rib 51 includes a set of upper teeth 53 and the lower side of the rib 51 includes a set of lower teeth 53A. The indicator wheel 50 has a pair of tabs, an upper tab 57 and a lower tab 57A. The upper tab 57 extends radially outward from the indicator wheel 50 above the rib 51 and the lower tab 57A extends radially outward from the indicator wheel 50 below the rib 51.

In operation, the force applied to the top of the outer cover 20 to release medication, serves to move the outer cover 20 and the indicator wheel 50 together. This relative movement of the outer cover 20 and indicator wheel 50 together causes the lower tab 57A of the indicator wheel 50 to ride on the ramp of a tooth of the lower set of teeth 53A of the rib 51. The riding of the lower tab 57A on the ramp incrementally rotates the indicator wheel 50 relative to the outer cover 20. When the lower tab 57A reaches the bottom of the ramp of the lower set of teeth 53A, the indicator wheel 50 and the outer cover 20 cannot move together any more, and the indicator wheel 50 cannot rotate any more in relation to the outer cover 20. When the force applied to the outer cover 20 is released, the outer cover 20 and indicator wheel 50 move apart (which movement, again, may be assisted by a flexible pawl or other spring-like element disposed between the indicator wheel 50 and the outer cover 20). This moving apart causes the upper tab 57 of the indicator wheel 50 to ride on the ramp of a tooth of the upper set of teeth 53 of the rib 51 of the indicator wheel 50. This riding of the upper tab 57 on the ramp produces another incremental rotation of the indicator wheel 50 relative to the outer cover 20.

Next described is an alternative embodiment for use with a different type of aerosol medication canister case. FIG. 5 shows the dispenser 112 with a canister case 116, a driver 170, an indicator wheel 150 and an outer cover 120. (For ease of reference, the 100-series labels of FIG. 5 generally correspond to the same labels of FIG. 1 without the first digit "1".) The canister case 116 is similar to the canister case 16 of the FIG. 1 previously described in that it has a canister case outlet 118 and a body to receive a canister 114. A key difference, however, as shown best in FIG. 5A, is that the canister case 116 extends to about the top of the canister 114 so that the top of the canister case 116 is approximately flush with the top of the canister 114. A cutout 115 is in the side wall of the canister case which is slightly larger than an ordinary index finger and another similar cutout is in the opposite side wall. To activate the device to release medication, it is necessary to place one's index finger over this cutout while applying an axial force urging the canister 114 downward into the canister case 116, so that the finger can move downward into the cutout 115 as the canister 114 moves downward. If one applies an axial force with one's finger positioned other than over the cutout 115, the upper edge of the canister case 116 will take the force, and the canister 114 will not properly descend into the canister case 116 to activate the internal valve to release a jet of the medication or to actuate the mechanism to advance the indicator wheel.

The driver 170 includes a skirt 172. Spaced around the inside surface of the skirt 172 is a set of several bumps 175 a having a thickness such that the skirt 172 can be snugly press-fitted over the canister 114 to hold the driver 170 onto the canister 114. It should be appreciated that the driver 170 could be replaced with the adhesive mount described in connection with FIG. 1 or some other mount and, likewise, the adhesive mount of FIG. 1 could be replaced with the press-fitted mount of FIG. 5.

Like the driver 70 of FIG. 1, the driver 170 of FIG. 5 includes an annular ring 175 above the base 172, with a set of upwardly protruding lugs 176. Each lug has a flexible lug body 177, a lug point 178 and a set of curved, flexible, upwardly extending pawls 180, all of which are essentially the same as in the embodiment of FIG. 1.

The indicator wheel 150 of the embodiment of FIG. 5 is essentially the same as the indicator wheel 50 of the embodiment of FIG. 1. It includes a top surface 152, a lower surface 154, a hole 156 through the middle, a set of upper surface teeth 158, and a set of lower surface teeth 160.

The outer cover 120 of the embodiment of FIG. 5 is somewhat similar to the outer cover 20 of the embodiment of FIG. 1, in that there is a roughly circular top 122, with a window 126 therethrough, an axially depending skirt 124 and a set of notches 129 spaced around the interior surface of the skirt 124. The axially depending skirt 124 differs from the axially depending skirt 24 of FIG. 1 in that the axially depending skirt 124 of the present embodiment is longer and includes a set of child resistant lugs 121 spaced around the radially inner surface thereof.

Figure 5B:
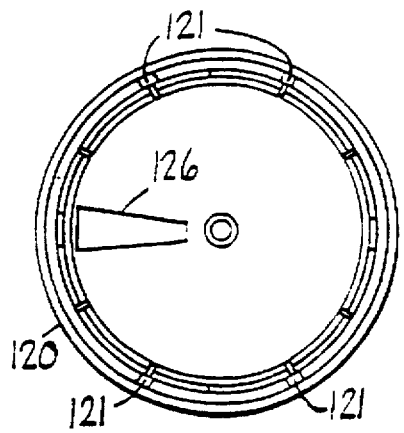
FIG. 5B is a bottom view of the outer cover of the invention.
Figure 5A:
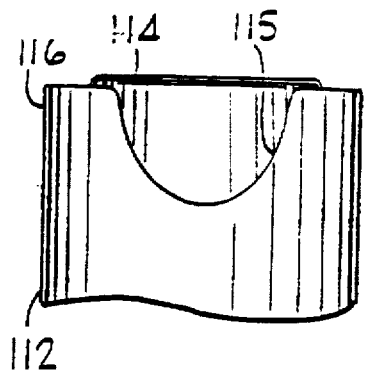
FIG. 5A is a side elevational view of a portion of canister and canister case used with an alternate embodiment of the invention.
Figure 5:
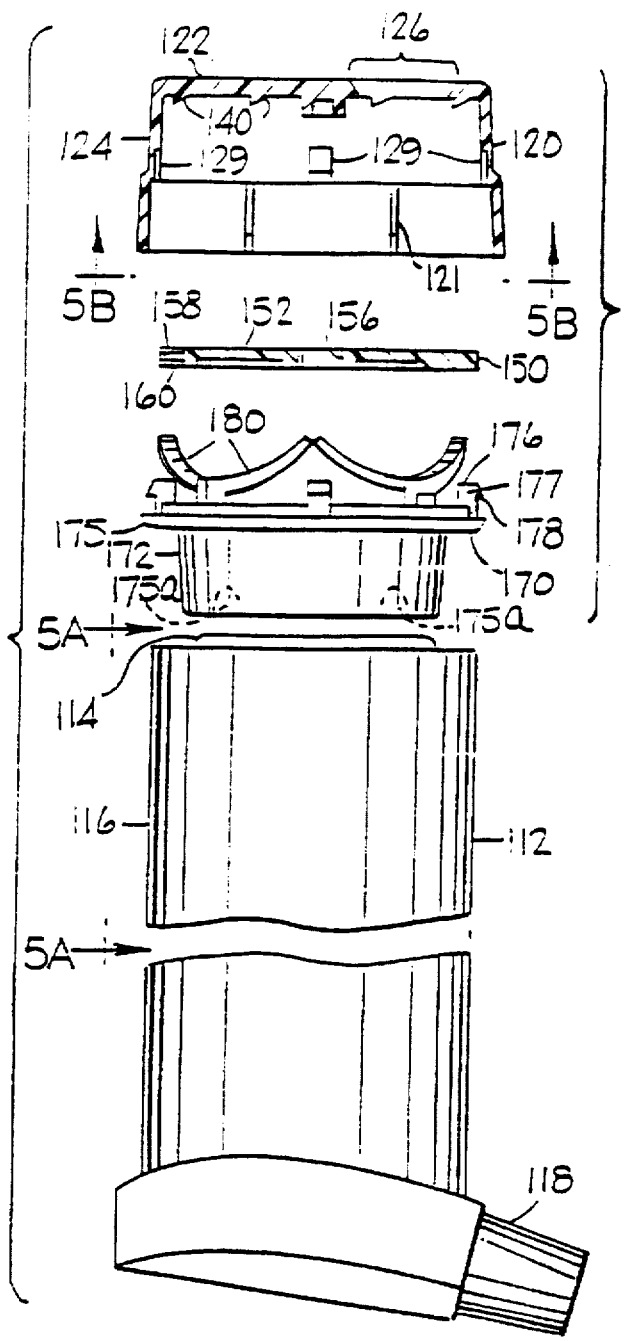
FIG. 5 is an exploded elevational view of an alternate embodiment of the present invention with a canister and canister case.

The child resistant lugs 129 are better shown in FIG. 5B, taken along line 5B—5B of FIG. 5. As can be appreciated from FIG. 5B, the child resistant lugs are not spaced equally, but instead there is a pair on one side and another pair on the opposite side. The two pairs of child resistant lugs 121 are spaced such that one pair can descend into the cutout 115 in the sidewall of the canister case 116 when the canister is depressed if that pair is centered over the cutout 115. At the same time, of course, the other pair descends into the cutout in the opposite sidewall. However, if the two pairs of child resistant lugs 121 are not centered over the cutouts, then the canister cannot be depressed to activate the valve in the canister case to release a jet of medication, because the child resistant lugs 121 will abut against the top of the canister case 116. Thus, to render the system child resistant, the device 110 is rotated along with the attached canister 114 a non-integral multiple of 180° after it is used so that the two pairs of child resistant lugs 121 are not aligned over the cutouts 115. The next time it is used, the device 110 along with the attached canister 114 must be rotated to re-align the pairs of child resistant lugs over the two cutouts 115. Only then can the device 110 descend over the canister case 116 while the child resistant lugs 121 descend into the cutouts 115. To tell the user when the pairs of child resistant lugs 121 are properly aligned over the cutouts 115 so that medication can be dispensed, there may be aligning arrows or other indicia (not shown) on the device 110 and the canister case 116.

Figure 6:
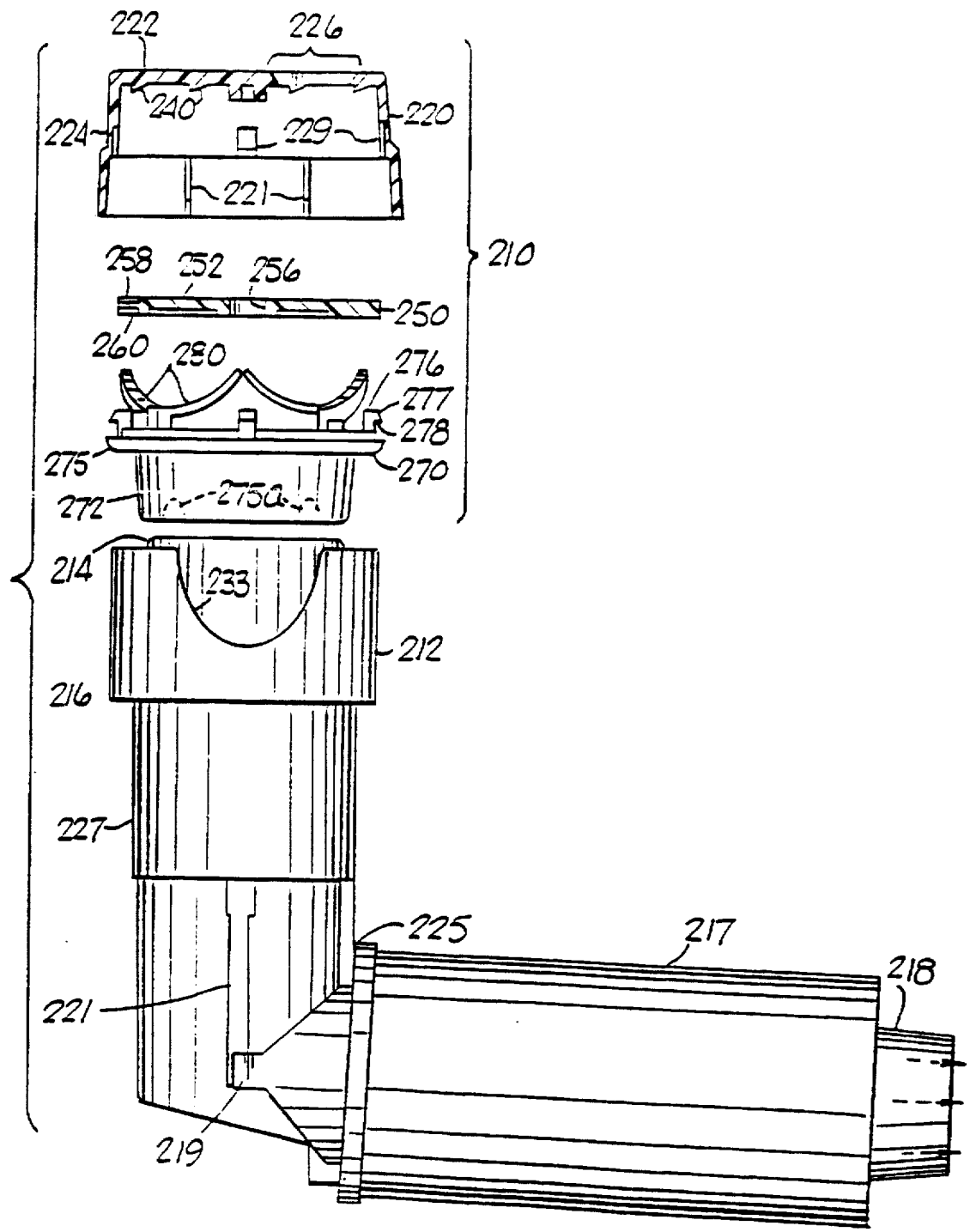
FIG. 6 is an exploded elevational view of an alternate embodiment of the present invention with a canister and canister case.

Next described is yet another alternative embodiment for use with still another aerosol medication canister case. FIG. 6 shows the dispenser 212 with a canister case 216, a driver 270, an indicator wheel 250 and an outer cover 220. The canister case 216 is a well known design in the art that is quite different from the canister cases 16 of FIG. 1 and 116 of FIG. 5 previously described. The canister case 216 includes a canister holder 227 and an aerosol chamber 217 with a dispensing mouth 218. The aerosol chamber 217 is a hollow cylinder which receives the canister holder 227 so that the entire canister case 216 collapses neatly into a package roughly the size of the aerosol chamber 217 when not in use. The canister case 215 includes a slot 221 in its lower portion which receives a tab 219 in the aerosol chamber 217. The canister case 215 also includes a longitudinal rib 223 which engages a notch 225 in the aerosol chamber 217 when the device is readied for use as explained below.

To use the device, the canister holder 227 is telescoped out of the aerosol chamber 217. The canister holder 227 and aerosol chamber 217 are hinged to a right angle as shown in FIG. 6 by rotating the aerosol chamber tab 219 in the canister holder slot 221, and the right angle arrangement is secured by allowing the canister holder rib 223 to engage the aerosol chamber notch 225. As mentioned above, the canister case 216 of the type shown in FIG. 6 is well known in the art and is in common use, and therefore it is not described in any additional detail here.

The invention 210 of FIG. 6 is essentially identical to the invention 110 of FIG. 5, in including a driver 270, an indicator wheel 250 and an outer cover 220, each of the same design as the driver 170, indicator wheel 150 and outer cover 120 of FIG. 5. (For ease of reference, the 200-series labels of FIG. 6 generally correspond to the 100-series labels of FIG. 5, wherein the last two digits are the same and the first digit is a "1" in FIG. 5 and a "2" in FIG. 6.)

The invention 210 is attached to the canister 214 by press-fitting the driver 270 onto the end of the canister 214 in the same manner as in the embodiment of FIG. 5. As can be seen in FIG. 6, the canister holder 216 includes a cutout 233 on one side and another cutout (not shown) on the other side. Like the cutout 115 of FIG. 5, the cutout 233 of FIG. 6 is designed to accommodate the user's finger when the canister 214 is depressed into the canister holder 227 to activate the internal valve to release a jet of medication. In the inventions of FIG. 5 and FIG. 6, however, that cutout is used to render the device child resistant. A set of two pairs of lugs 221 are on the interior surface of the skirt 224 of the outer cover 220. If each pair of lugs 221 is centered over a cutout 233, then the interior valve may be actuated to release medication by depressing the invention 210 downward toward the canister holder 227 so that the outer cover skirt 224 passes over the top of the canister holder 227 as each pair of lugs 224 descends into a cutout 233. However, if each pair of lugs 224 is not so centered over a cutout 233, then any attempt to actuate the internal valve to release a jet of medication, or to advance the indicator wheel by actuating the indicator mechanism, will be blocked by the lugs 224 abutting against the top of the canister holder 227. Thus, the device is rendered child resistant because the user must be certain that there is proper alignment between the invention 210 and the canister holder 216 (such as by lining up alignment marks that are not shown). This is an action that cannot normally be accomplished by young children.

Another means for making the device child-resistant involves the length of the depending skirt 224 of the outer cover 20. As explained above, the canister holder 227 telescopes out of the aerosol chamber 217 and then hinges to a roughly right angle to dispense medication. After the medication is dispensed, the canister holder 227 is collapsed back into the aerosol chamber 217. However, even in the collapsed state, medication can be dispensed by the user or by a child if the dispenser does not include the indicator device of the present invention, by simply pressing the end of the canister 214. This can be prevented by using the indicator device of the present invention and lengthening the depending skirt 224 to such an extent that it abuts against the end of the aerosol chamber 217 when the canister holder 227 is collapsed into the aerosol chamber 217, so that any force applied to the outer cover 220 is resisted by the aerosol chamber 217 and not transferred to the canister 214 to dispense medication. When the device is readied for use, the canister holder 227 is telescoped out of the aerosol chamber 217 and hinged to a right angle thereto, so that the outer cover skirt 224 no longer abuts against the end of the aerosol chamber 217, to allow a force applied to the outer cover 229 to be transferred to the canister 214 to actuate the internal valve and release the medication.

What is claimed is:

1. A device to indicate the release of aerosol medication from a canister wherein aerosol medication is released from the canister by applying a force to the canister, comprising a dispenser including a canister case for holding the canister and indicator which advances upon the application of said force to indicate a release of the aerosol medication;

the indicator including an outer cover, an indicator wheel engaged with the outer cover, and a driver engaged with the outer cover and indicator wheel to translate an aerosol releasing non-rotative force on the outer cover into a rotation of the indicator wheel relative to the outer cover to indicate the release of the aerosol medication;

the outer cover including a top portion and a depending skirt, and the indicator wheel is nested in the outer cover depending skirt, and the indicator further including a retainer nested in the outer cover depending skirt so that the indicator wheel is disposed between the outer cover top portion and the retainer;

the dispenser and indicator including a child resistant element to resist the releasing of aerosol medication by a child including at least one protrusion on one of the outer cover depending skirts and the dispenser and a protrusion-mate on the other of the outer cover depending skirt and the dispenser to mate with the protrusion to allow a force applied on the indicator to be translated to the canister only if the protrusion and protrusion mate are aligned.

2. The device of claim 1, wherein the outer cover depending skirt extends over a portion of the canister case when said force is applied to release aerosol medication and said protrusion is a protrusion on the depending skirt extending radially inward, and the protrusion mate is a cutout in said canister case, whereby the outer cover skirt is free to extend over a portion of the canister case to allow aerosol medication to be released when the protrusion is aligned with the cutout but is not free to extend over a portion of the canister case to allow aerosol medication to be released when the protrusion is not aligned with the cutout.

3. A device to indicate the release of aerosol medication from a canister wherein aerosol medication is released from the canister by applying a force to the canister, comprising a dispenser including a canister case for holding the canister and indicator which advances upon the application of said force to indicate a release of the aerosol medication;

the indicator including an outer cover, an indicator wheel engaged with the outer cover, and a driver engaged with the outer cover and indicator wheel to translate an aerosol releasing non-rotative force on the outer cover into a rotation of the indicator wheel relative to the outer cover to indicate the release of the aerosol medication;

the outer cover including a top portion and a depending skirt, and the indicator wheel being nested in the outer cover depending skirt, and the indicator further including a retainer nested in the outer cover depending skirt so that the indicator wheel is disposed between the outer cover top portion and the retainer;

the dispenser including an aerosol chamber slidably attached to the canister case whereby the canister case slides into a the aerosol chamber in a first position for storing the dispenser and the canister case slides out of the aerosol chamber in a second position for releasing aerosol medication;

wherein the aerosol chamber includes one end having a rim, and wherein the rim and the outer cover depending skirt are configured such that the rim abuts the depending skirt to prevent the release of aerosol medication when the dispenser is in said first position but does not abut the depending skirt to prevent the release of medication where the dispenser is in said second position.

4. The device of claim 3, wherein the canister case has an end with an opening and the indicator device is attachable to the canister through said canister case opening, and the canister includes a release valve actuatable upon depressing the canister into the canister case, and the indicator is attachable to the canister, whereby the canister is depressed into the canister case by applying a force to the indicator, said force being resisted by the aerosol chamber rim when the dispenser is in said first position but not resisted by the aerosol chamber rim when the dispenser is in said second position.

* * * * *